(12) United States Patent
Mitchell et al.

(10) Patent No.: US 10,967,158 B1
(45) Date of Patent: Apr. 6, 2021

(54) CEREBRAL SHUNT VALVE

(71) Applicant: POPFLOW, LLC., Hanover, NH (US)

(72) Inventors: Scott C. Mitchell, Indianapolis, IN (US); David Frederick Bauer, Hanover, NH (US); Gabriella L. Grangard, Jupiter, FL (US); Waad Kahouli, Hammam Sousse (TN); Christopher C. Dalldorf, Greensboro, NC (US)

(73) Assignee: PopFlow, LLC, Hanover, NH (US)

( * ) Notice: Subject to any disclaimer, the term of this patent is extended or adjusted under 35 U.S.C. 154(b) by 431 days.

(21) Appl. No.: 15/188,947

(22) Filed: Jun. 21, 2016

(51) Int. Cl.
*A61M 27/00* (2006.01)
*A61M 39/24* (2006.01)
*A61M 39/22* (2006.01)

(52) U.S. Cl.
CPC .......... *A61M 27/006* (2013.01); *A61M 39/24* (2013.01); *A61M 2039/226* (2013.01); *A61M 2205/18* (2013.01); *A61M 2205/3306* (2013.01); *A61M 2205/3331* (2013.01); *A61M 2205/3344* (2013.01); *A61M 2205/52* (2013.01); *A61M 2205/702* (2013.01)

(58) Field of Classification Search
CPC .............. A61M 27/006; A61M 39/24; A61M 2205/3344; A61M 2205/3331; A61M 2205/3334; A61M 2039/242; A61M 2039/2426; A61M 2202/0464; A61M 39/22

See application file for complete search history.

(56) References Cited

U.S. PATENT DOCUMENTS

| 274,447 | A | 3/1883 | Kennish |
| 3,654,932 | A | 4/1972 | Newkirk et al. |
| 5,205,834 | A | 4/1993 | Moorehead et al. |
| 6,427,874 | B2 * | 8/2002 | Brown ............... B65D 47/2031 220/203.11 |
| 8,206,334 | B2 | 6/2012 | Kralick et al. |
| 8,328,769 | B2 | 12/2012 | Dikeman et al. |
| 8,480,612 | B2 | 7/2013 | Kassem |
| 8,894,584 | B2 | 11/2014 | Swoboda et al. |
| 9,044,541 | B2 | 6/2015 | Blanchard et al. |
| 2006/0020239 | A1 | 1/2006 | Geiger et al. |
| 2009/0053081 | A1 * | 2/2009 | Griffiths .............. F04B 43/0054 417/413.1 |

(Continued)

*Primary Examiner* — Kai H Weng
(74) *Attorney, Agent, or Firm* — Loginov & Associates, PLLC; William A. Loginov

(57) ABSTRACT

A bi-stable popper valve and a device for detecting blockage in a flow of a fluid are provided. The valve includes a membrane supporting two conformations: in a first conformation the membrane is convex in relation the upstream fluid, and in a second conformation the membrane can be concave in relation to the upstream fluid, such that in the first conformation the flow of the fluid through the membrane is prevented and in the second conformation the flow of the fluid through the membrane is permitted through an pore defined by the membrane in only the second conformation. The membrane changes from the first conformation to the second responsive to a pressure of the fluid meeting or exceeding an opening pressure value of the membrane. A sensor can detect a shift from the first conformation to the second conformation, indicating a flow, or absence of flow, of the fluid.

20 Claims, 9 Drawing Sheets

(56) References Cited

U.S. PATENT DOCUMENTS

| | | |
|---|---|---|
| 2014/0243703 A1 | 8/2014 | Schmidt et al. |
| 2016/0045629 A1* | 2/2016 | Gardner ............... A61L 2/18 422/292 |

* cited by examiner

CEREBRAL SHUNT VALVE

FIELD OF THE INVENTION

The present disclosure relates to a flow valve and, more particularly, to a flow valve that may be used in a cerebral shunt.

BACKGROUND OF THE INVENTION

Hydrocephalus is a medical condition characterized by accumulation of excess cerebrospinal fluid (CSF) (also referred to as cerebral spinal fluid) in the brain. The accumulation of CSF leads to an increase in intracranial pressure (ICP). Elevated ICP results in clinical symptoms such as headache, sleepiness, and vomiting. If untreated, rising ICP will cause brain damage, and ultimately, death. Though there is currently no known cure for hydrocephalus, the current treatment is to surgically implant a cerebral shunt, which diverts the flow of excess CSF from the cranium to another area of the body where the CSF can be reabsorbed.

There are two major types of cerebral shunts: non-programmable shunts and programmable shunts. Non-programmable shunts have a single valve pressure, and programmable shunts allow medical professionals to noninvasively adjust valve pressure. Regardless of the type of cerebral shunt, almost all include a ventricular catheter, a flow valve, and a distal catheter.

Implanted shunts have an approximately 50% failure rate in the first four years, typically caused by a blockage in the cerebral shunt. After placement of the cerebral shunt, there is no way to preemptively detect whether there is a blockage (from, for example, brain tissue or a break in a catheter) in the shunt before the appearance and progression of pronounced symptoms, such as headaches, vomiting, or nausea. Many patients with implanted shunts are nonverbal and are thus unable to communicate symptoms to caregivers, further complicating the diagnosis of shunt failures. Even with apparent symptoms, it is difficult to discern whether these symptoms correspond to an illness such as influenza or shunt failure, and in many cases there is no detectable anatomical changes by which to indicate shunt failure. As such, when a patient with a cerebral shunt experiences any of these symptoms, the person may be hospitalized and monitored for deterioration of symptoms, examined by physicians using a non-invasive technique such as comparative imaging, or taken immediately into an operating room where a physician may use an invasive surgery to detect a shunt malfunction and/or replace the cerebral shunt.

Non-invasive detection methods typically include cranial imaging with computed tomography (CT) or magnetic resonance imaging (MRI), radiographs of the implanted tubing evaluating for disruption, and physical examination. Other non-invasive studies such as transcranial doppler, tympanic membrane displacement, and optic nerve sheath diameter measurement have proven unreliable. Even CT and MRI imaging are unable to detect elevated ICP in over thirty percent (30%) of surgically documented shunt malfunction cases because the size of the ventricles does not enlarge in every patient with a shunt malfunction. Invasive detection methods of shunt malfunction besides surgical shunt exploration include the implantation of a ventriculostomy or fiber-optic strain gauge to measure intracranial pressure. The invasive detection methods require surgery, which introduces the risk of complication such as infection and hemorrhage and is both costly and traumatic for a patient. Given the high failure rates of shunts, there is a compelling need for a new shunt design with a lower failure rate. Due to the drawbacks of non-invasive and invasive detection methods of cerebral shunt failure, there is also a need to differentiate cerebral shunt failure from non-life threatening illnesses. In addition, the early detection of shunt failure could lead to early intervention, mitigating the risks of headache, nausea, emesis, lethargy, and even death in a patient with an acute shunt malfunction.

SUMMARY OF THE INVENTION

This present disclosure overcomes disadvantages of the prior art by providing an apparatus and system for allowing the one-way flow of CSF through a shunt and away from the brain. A PopFlow popper membrane utilizes a passive bi-stable membrane system that uses the properties of dynamic permeability to allow intermittent draining of excess CSF through the shunt and away from the brain. Embodiments of the present disclosure also address deficiencies of the art in respect to non-surgically detecting cerebral shunt failure and provide a novel and non-obvious device for detecting cerebral shunt failure due to blockage.

In an illustrative embodiment, a valve popper can include a resilient membrane having at least one pore extending between a first side of the membrane and a second side of the membrane. When a fluid facing a first side of the membrane is under a lower pressure, the membrane is in a first conformation. In the first conformation, the first side of the membrane is convex and at least one pore is closed. When the fluid facing the first side of the membrane is under a higher pressure, the membrane flexes to a second conformation. When the membrane is in the second conformation the first side of the membrane is not convex and the at least one pore is open allowing the fluid to flow through the membrane. When the fluid facing the first side of the membrane is under the lower pressure the membrane can have a dome shape. When the fluid facing the first side of the membrane is under the higher pressure, the second side of the membrane can be convex. The popper can include a brim extending outwardly from the perimeter of the membrane at a base of the membrane. When the fluid facing the first side of the membrane is under the higher pressure, the membrane flexes to the second conformation and the at least one pore opens, so that the fluid flows through the open pore to a second side of the membrane. When this happens the pressure of the fluid facing the first side of the membrane drops to the lower pressure so that the membrane returns to the first conformation where the first side of the membrane becomes convex and the at least one pore becomes closed. A pore can be defined by at least one slit. A pore can be defined by at least two slits that intersect each other.

In an illustrative embodiment, a valve can include a valve housing defining an upstream portion and a downstream portion, and a popper between the upstream portion and the downstream portion. The popper can include a resilient membrane having at least one pore extending between a first side of the membrane and a second side of the membrane, with the first side of the membrane facing towards the upstream portion. The popper can form a seal between the upstream portion and the downstream portion. When a fluid facing a first side of the membrane is under a lower pressure, the membrane is in a relaxed state where the first side of the membrane is convex and the at least one pore is closed. When the fluid facing the first side of the membrane is under a higher pressure, the first side of the membrane is not convex and the at least one pore is open allowing the fluid to flow through the membrane. The membrane can have a dome shape when the fluid facing the first side of the membrane is under the lower pressure. The second side of the membrane can be convex when the fluid facing the first side of the membrane is under the higher pressure. The popper can include a brim extending outwards from a perimeter of the membrane at a base of the membrane. At least one pore can be defined by at least one slit. At least one pore can be defined by at least two slits that intersect each other.

In an illustrative embodiment, the device for detecting blockage in a vessel can include a popper extending entirely across a cross sectional area of a housing and forming a seal between an upstream portion of the housing and a downstream portion of the housing. The valve can include a membrane supporting two conformations. A first of the conformations may include where the membrane is convex in relation to the upstream portion of the housing, and a second of the conformations may include where the membrane is concave in relation to the upstream portion of the housing. The resilient membrane can define at least one pore through the membrane, the pore being closed in the first conformation and the pore being open in the second conformation, such that in the first of the conformations the flow of a substance through the membrane may be prevented and in the second of the conformations the flow of the substance through the membrane may permitted through the pore defined by the membrane that is open in the second conformation. The device can further include one or more sensors coupled to the housing. The one or more sensors detect changes of the membrane from the first of the conformations to the second of the conformations. Further, the membrane changes from the first conformation to the second conformation responsive to a pressure of the substance in the upstream portion of the housing meeting or exceeding an opening pressure value of the membrane. At least one sensor can include a light emitter, where a path of the light from the light emitter to the light detector is blocked by the membrane in only one configuration. At least one sensor can be a variable bending resistor that can sense the movement of the membrane between the first configuration and the second configuration. A memory storage device may be included that receives data from the one or more sensors. The memory storage device can store binary data received from the one or more sensors, where each binary data point can indicate the membrane being in a first conformation or a second conformation. A timing device may be included that sends a signal to the sensor, so that when the sensor receives a signal from the timing device, the sensor senses whether the membrane is in the first conformation or the second conformation.

Additional aspects of the disclosure will be set forth in part in the description which follows, and in part will be obvious from the description, or may be learned by practice. The aspects of the disclosure will be realized and attained by means of the elements and combinations particularly pointed out in the appended claims. It is to be understood that both the foregoing general description and the following detailed description are exemplary and explanatory only and are not restrictive of the claims.

BRIEF DESCRIPTION OF THE DRAWINGS

The invention description below refers to the accompanying drawings, of which.

DETAILED DESCRIPTION

Embodiments of the disclosure provide an apparatus and system for safely releasing excess CSF pressure from within the brain by allowing the one-way flow of CSF away from the brain through a cerebral shunt. Further embodiments also provide for detecting cerebral shunt failure due to blockage.

Figure 1:
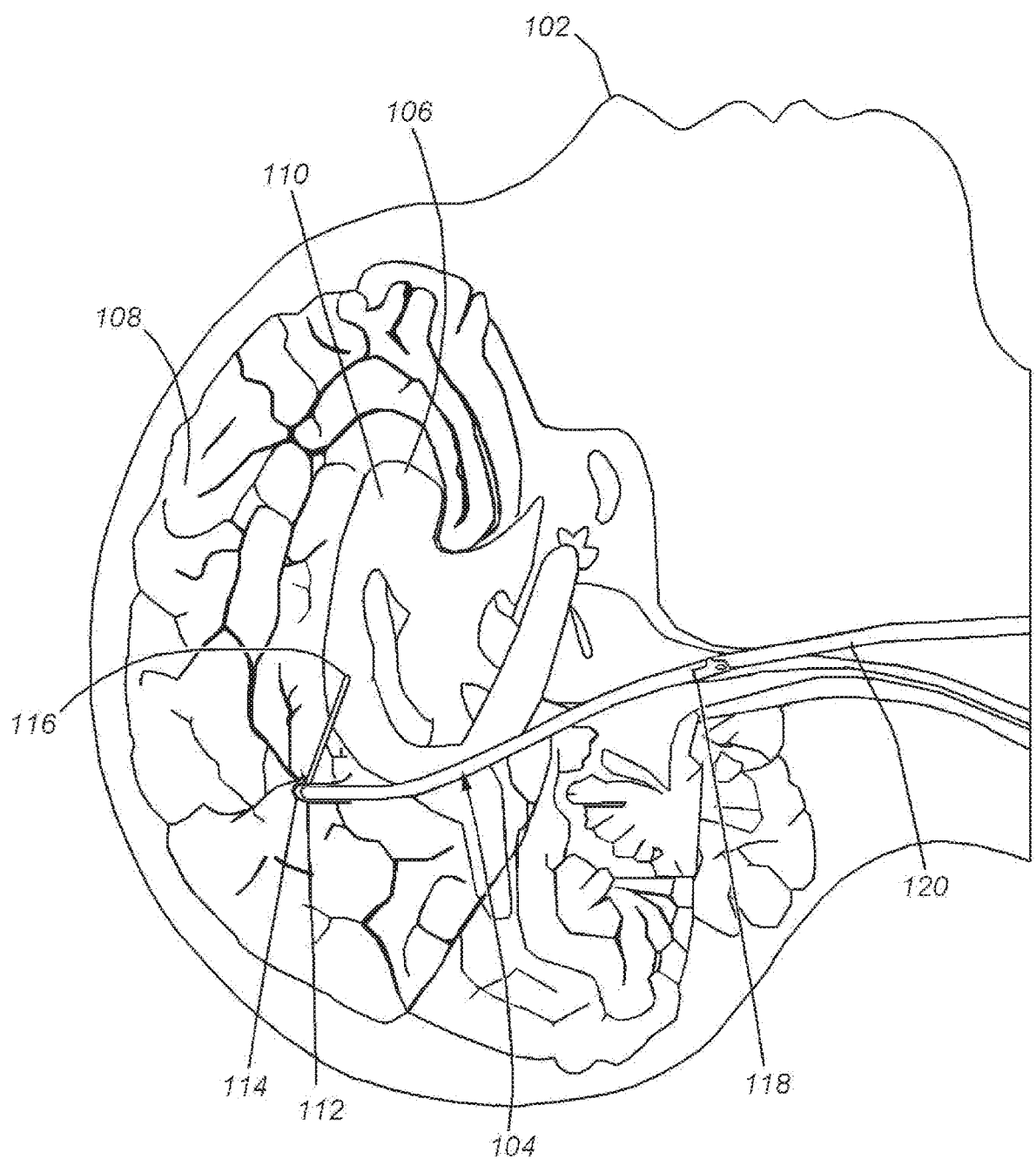
FIG. 1 is a cross sectional view of a patient with an implanted cerebral shunt.

FIG. 1 is a cross-sectional view of a hydrocephalus patient 102 with a non-limiting example of an embodiment of a cerebral shunt 104. Healthy CSF pressure may be approximately 5-15 mmHg. Hydrocephalus patients with an excess of CSF 106 in the brain 108 often have enlarged ventricles 110, filled with CSF 106, as shown. The excess of CSF 106 can create an elevated pressure in the brain that can result in enlarged ventricles 110. A cerebral shunt 104 can be implanted in the patient 102 allowing drainage of excess CSF 106. The cerebral shunt 104 can include a ventricular catheter, a valve, and a distal catheter. The ventricular catheter 112 can be inserted into the cranium through cranium entry point 114. A proximal end 116 of the ventricular catheter 112 can be implanted into the ventricle 110 to allow drainage of excess CSF 106. Excess CSF 106 can drain from the ventricle 110 into the proximal end 116 of the ventricular catheter 112 and through the ventricular catheter 112 to a valve 118. Valve 118 can permit CSF 106 to flow through the valve 118 and away from the brain 108 when the accumulation of excess CSF 106 causes an elevation of pressure. The elevated pressure of the CSF 106 can trigger the valve 118 to open and allow excess CSF 106 to flow away from the brain 108. When the valve 118 is open, CSF 106 can flow through the valve and into a distal catheter 120. The CSF 106 can then flow through the distal catheter 120 and into a region of the body of the patent 102 that can safely absorb the excess CSF 106. By way of non-limiting example, the CSF 106 can flow into the peritoneal cavity (not shown) that can have a pressure of approximately 4-6 mmHg. Alternately the CSF 106 could flow into the right atrium of the heart, or other regions with pressures that can be lower than the pressure in the brain 108. It is important that the valve 118 allows drainage of only the excess CSF 106, while leaving an appropriate volume of CSF 106 in the brain 108. It is also important that the valve 118 does not permit backflow of fluids from another part of the body to flow backwards through the shunt 104 and into the brain 108, but instead allows only the one-way flow of CSF 106 away from the brain 108.

Figure 2A:
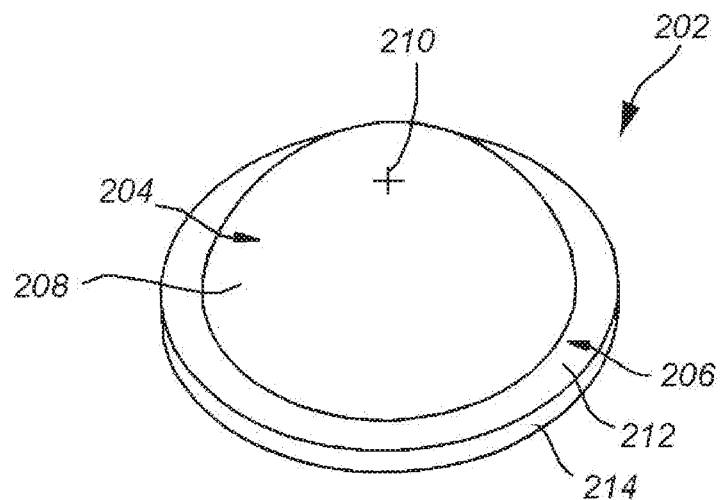
FIG. 2A is a perspective view of an exemplary popper for use in a one-way cerebral shunt valve according to an embodiment.

FIG. 2A is a perspective view of an exemplary popper 202 for use in a novel one-way cerebral shunt valve (described below). Popper 202 can be made of a resilient material and can include a membrane 204 and a brim 206. Membrane 204 is shown in a relaxed, dome-shaped, closed conformation, and includes a proximal surface 208 and a distal surface (not shown). Membrane 204 is shown with a pore formed by two slits 210 that cut through the membrane 204 between the proximal surface 208 and the distal surface (not shown). The two slits 210 are depicted perpendicular to each other, but different numbers of slits, alternate arrangements of slits, or different pore shapes are specifically contemplated. In alternate embodiments, the membrane 204 can have three slits 210 that can be in an asterisk-shaped formation, four or more slits 210, or other shapes of cuts through the membrane 204. Brim 206 can have a proximal face 212, an outer face 214, and a distal face (not shown). Popper 202 is designed to be a component of a novel one-way cerebral shunt valve as described below.

In accordance with an embodiment of the disclosure, when the CSF pressure in a cerebral shunt and, in particular, in a ventricular catheter of the cerebral shunt, is greater than a triggering pressure of a bi-stable popper within a valve coupled to the cerebral shunt, the valve is activated. The activation of the bi-stable popper causes a deformation change of the popper. The resulting deformation change causes the popper to invert from a closed upstream position, where the flow of CSF is prevented, to an open downstream position, where the flow of CSF is permitted through an opening defined by the membrane. In the closed upstream position, the proximal surface of the membrane is convex to the CSF entering the valve from the brain, and in the downstream position the proximal surface is not convex to the CSF entering the valve from the brain, and can be concave to the CSF entering the valve from the brain. Once the CSF pressure in the ventricular catheter is no longer greater than the triggering pressure of the popper, the popper reverts to its original closed upstream configuration. Additionally, the displacement of the membrane between the closed upstream conformation to an open downstream conformation can be measured by a sensing mechanism coupled to the valve. In this way, failure of a cerebral shunt due to blockage can be detected, because if the valve fails to open, then it can be inferred that there is a blockage along the flow of CSF.

The membrane 204, in one embodiment, is substantially hemispherical (semispherical) as well as symmetrical, but, in a different embodiment, the membrane 204 can also be asymmetrical about a center axis or a plane. In yet a different embodiment, the membrane 204 can be ellipsoidal or conical as well as have other two or three-dimensional geometries. In yet another different embodiment, the membrane 204 can be a spherical cap or other various dome shapes. In other words, the membrane 204 can be volumetric. In yet a different embodiment, the membrane can have a wart-like bump or bumps (or nipple(s) or protrusion(s)) being outwardly projected from a surface of the membrane 204. Of note, in an embodiment, the wart-like bump can be part of a sensing mechanism (see FIGS. 9A and 9B). Additionally, the membrane 204 can be axisymmetric. In some embodiments of the popper 202, the membrane 204 can define an opening, or pore, originating at the apex 222 of the membrane 204. In other embodiments of the popper 202, the opening can be positioned at any other point on the membrane 204. In other embodiments more than one pore may be present through the membrane. As explained below and illustrated in FIGS. 3B and 3D, the pore, or opening 310 defined by the membrane 204 permits flow of CSF through the pore, or opening, when the pressure of the CSF upstream from the popper exceeds the popping pressure (triggering pressure) of the popper 202. The membrane 204 is further encircled by a brim 206 ((outer ring or annulus (annulus)) encompassing a portion of or the entirety of the periphery (perimeter) of the base of the volumetric shape of the membrane 204. Of note, the popping pressure or triggering pressure refers to a value equal to an amount of pressure that, when applied to the proximal upstream surface of the membrane 204, induces a buckling, or inverting, of the membrane 204 to a different conformation. In other words, the popping pressure refers to the amount of pressure required to cause the membrane 204 to change from one conformation (such as a closed conformation) to a second conformation (such as an open conformation). Of further note, the popping pressure value at which the membrane 204 changes from a closed conformation to an open conformation can also be referred to as an opening pressure. Similarly, the popping pressure value at which the membrane 204 changes from an open conformation to a closed conformation can also be referred to as a closing pressure. Typically, the closed conformation is when the proximal surface 208 of the membrane 204 is convex to the CSF entering the valve from the brain. The open conformation is when the proximal surface 208 of the membrane 204 is not convex to the CSF entering the valve from the brain (not convex to the positive pressure difference), and can be concave to the CSF entering the valve from the brain, or positive pressure difference. Further, both the closed conformation and also the open conformation are stable states. As such, the popper 202 can be said to be bi-stable.

Figure 2B:
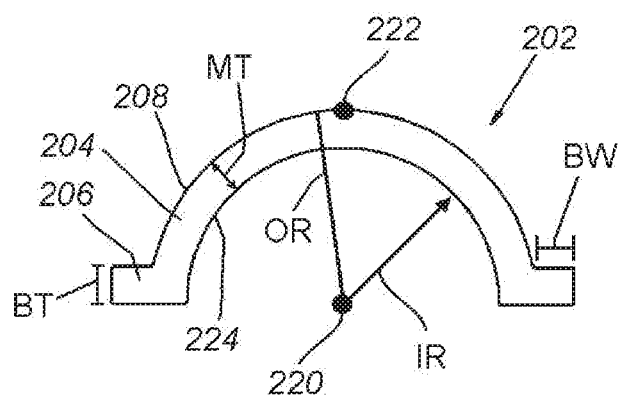
FIG. 2B is a cross sectional view of the popper of FIG. 2A.

More specifically, as illustrated in FIG. 2B, in one embodiment the popper 202 can include a center 220 and an apex 222 as well as an inner or internal radius IR and an outer radius OR. The proximal surface 208 of the membrane 204 is shown as convex, and the distal surface 224 of the membrane 204 is shown as concave in this conformation. The center 220 can be the geometric center of the sphere forming the substantially hemispherical membrane 204. The measured difference between the internal radius IR and the outer radius OR is equivalent to the thickness MT of the membrane 204. In an embodiment, membrane 204 can also be described as having a principal radius of curvature, which is equivalent to the internal radius IR, and having a thickness MT. Though not illustrated, it is contemplated that the thickness MT does not have to be constant. In other words, the thickness MT can vary from the base of the membrane 204 (the intersection of where the membrane 204 meets the brim 206) to the apex 222 of the membrane 204. The ring or brim 206 can also include a brim width BW and brim thickness BT: each can vary in size. In one embodiment, the thickness 230 can be 0.5 millimeters (mm), the internal radius IR can be 5 millimeters (mm), the brim thickness 256 can be 1 mm and the brim width 255 can be 1 millimeter (1 mm) but the thickness MT, the brim thickness BT, brim width BW and the internal radius IR can vary. For example, the thickness BT can be in the range of about 0.5 mm to 1 mm. But, it is further noted that the dimensions of the popper 202 can further vary depending on use. More specifically, when the popper 202 is used to monitor the flow of gas and/or liquids in pipes in a dwelling or industrial setting, the dimensions of the popper 202 will be larger to accommodate the larger size of the pipes and also the higher flow pressures experienced by the popper 202. In a different embodiment, the popper 202 may include no brim 206. In other words, in some embodiments of the popper 202, there may be no brim 206 and only the membrane 204. More specifically, in an embodiment, the brim 206 may not be necessary in applications where the popper 202 is fused and/or manufactured directly into the walls of a catheter, tube, pipe, or housing (see FIG. 6B).

The popper 202 can be made from a single material, i.e. have a uniform composition, or the popper 202 can be made from a variable polymer composition (a combination of different materials). More specifically, the materials from which the popper 202 can be manufactured from are, but are not limited to, nylon, polyethylene, polyester, urethane, and rubber, including silicone. In a preferred embodiment, the popper 202 is made from silicone rubber. Additional materials, such as metal powders and/or graphite, can be homogenized with the silicone rubber or as a film on or inside the rubber (or any material from which the popper 202 is made). With respect to the size of the popper 202, the preferable overall dimensions of the popper 202 can vary depending on use, but with respect to use in conjunction with a cerebral shunt, it is contemplated that the overall diameter of the popper 202 in one embodiment, including the brim 206 is between one millimeters and seven millimeters (1 mm-7 mm). In a different embodiment, the overall diameter of the popper 202 including the brim 206, if such is present, is less than 3.5 centimeters. In an embodiment, the diameter of the popper 202 (including the diameter of the membrane 204 as well as the brim width BW) can be sized to create a friction fit between popper 202 and the inner walls of a cerebral shunt valve. In other words, the popper 202 can be sized to fit snugly in between the walls of a cerebral shunt valve. In this way, the position of the popper 202 in the cerebral shunt valve creates a seal preventing the flow of CSF at the boundary between the popper 202 and the inside surface of the cerebral shunt valve. It is further contemplated that the popper 202 can also be coupled to a valve by glue, clamped in place, and/or via a gasket. For example, if the popper 202 is used to monitor flow of gas through pipes in a house, the popper may be secured to one of the pipes by bonding cement. Yet further, the popper 202 can be manufactured using any technique now known or later developed, including, but not limited to molding, including injection molding and 3-D printing. Yet even further, the popper 202 can be fabricated so it is directly integrated with a valve and/or other vessel that permits flow of gas and/or liquid, such as a pipe or housing, so that no brim 206 is necessary to create a seal or friction to hold the popper in place. It is further contemplated that the popper 202 can be chemically bonded to the vessel wall. Additionally, it is further contemplated that the popper 202 and/or a valve in which the popper 202 is disposed may be impregnated with antibiotic resistive chemicals or drugs, such as barium, to reduce infection rates, for example, in medical applications.

Figure 3A:
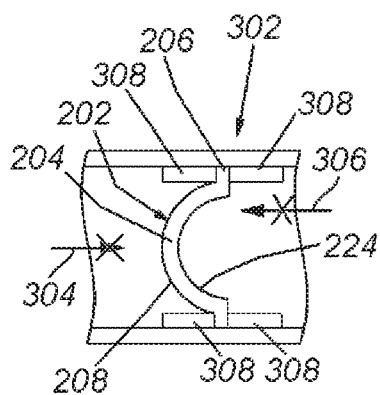
FIG. 3A is a cross sectional view of an exemplary valve with the popper of FIG. 2A shown in a closed conformation according to an embodiment.
Figure 3B:
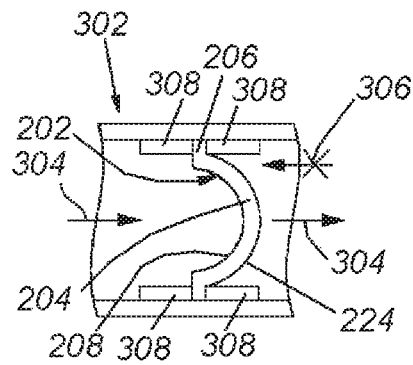
FIG. 3B is a cross sectional view of the exemplary valve of FIG. 3A with the popper of FIG. 2A shown in an open conformation according to the embodiment, when upstream fluid pressure exceeds the opening pressure of the popper of FIG. 2A.

FIG. 3A is a cross sectional view of an exemplary valve with the popper of FIG. 2A shown in a closed conformation according to an embodiment. FIG. 3A illustrates how the popper 202 (shown as a cross section) is configured to prevent the flow of CSF through the valve 302 when the upstream CSF pressure in the ventricular catheter is less than a popping pressure, where the popping pressure is the amount of upstream CSF pressure in the ventricular catheter required to cause a configuration change of the popper 202. More specifically, when the upstream CSF pressure in the ventricular catheter is less than the popping pressure, the popper 202 is impermeable and remains in a closed upstream position, as shown in FIGS. 3A and 3B. In other words, when the CSF pressure is below the popping pressure of popper 202, there is no flow of CSF through the popper 202 having a membrane 204 and brim 206. Therefore, the popper 202 remains in its original, relaxed configuration, such as in a closed upstream position (the proximal surface 208 of membrane 204 is convex toward CSF entering the valve 302) (see FIG. 3A). Of note, upstream refers to the orientation of the popper 202 in relation to the flow of CSF. As the popper 202 in FIG. 3A is oriented against the flow (but not backflow) of CSF, where the membrane 204 is convex in relation to a direction of the flow of CSF (or any substance), the popper 202 can be described as being in an upstream position. Further, as the popper 202 pictured in FIG. 3A prohibits the flow of CSF, the popper 202 is also considered closed.

Figure 3C:
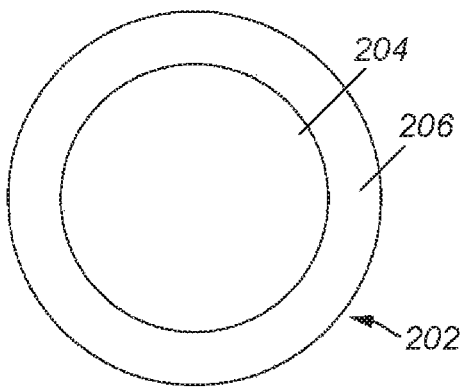
FIG. 3C is a plan view of the popper of FIG. 3A in a closed position.
Figure 3D:
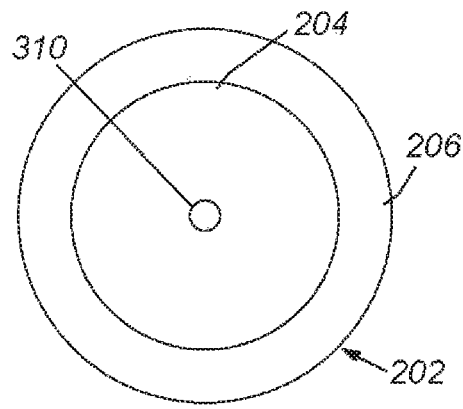
FIG. 3D is a plan view of the popper of FIG. 3B in an open position.
Figure 3E:
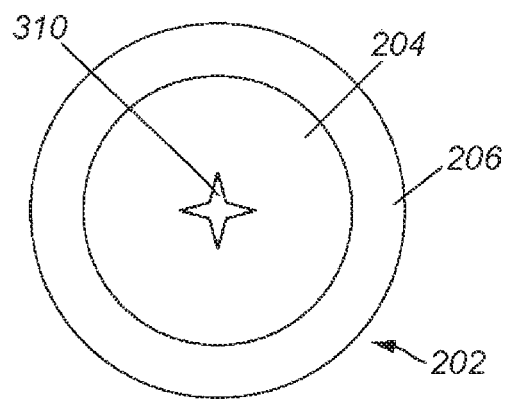
FIG. 3E is a plan view of an alternate embodiment of the popper of FIG. 3B in an open position.

But when the CSF pressure on the proximal surface 208 of the membrane 204 is equal to or greater than the popping pressure of the popper 202, the popper 202 undergoes a conformational change, as shown in FIG. 3C (which shows the popper 202 in cross section), that allows the flow of CSF through an opening 310 in popper 202 having a membrane 204 and brim 206 (see FIGS. 3D and 3E). In other words, the popper 202 undergoes a conformation change resulting in the membrane 204 of the popper 202 inverting from a closed upstream position convex toward CSF entering the valve 302 to an open downstream position concave to the CSF entering the valve 302. The value at which the popper 202 undergoes the conformation change from closed to open can also be referred to as an opening pressure. In practice, it is the membrane 204 that undergoes the conformation change, not the brim 206. Of note, downstream refers to the orientation of the membrane 204 in relation to the flow of CSF. As the membrane 204 in FIG. 3C is oriented with the flow (but not the backflow) of CSF, the popper 202 can be described as being in a downstream position. In other words, downstream refers to the membrane 204 of the popper 202 being orientated concave in relation to the CSF entering the valve 302. Further, as the popper 202 pictured in FIG. 3C permits the flow of CSF, the popper 202 is also considered open.

Further, as illustrated in FIGS. 3A and 3C, the flow of CSF (or any substance) is indicated by arrow 304, whereas when arrow 304 also includes an "X" this indicates no flow. Additionally, arrow 306 indicates the direction of backflow, and is illustrated with an "X" showing that the valve does not permit backflow. Further, FIGS. 3A and 3C illustrate, in one embodiment, that the popper 202 can be held in place in the valve 302 or any vessel via one or more clamps 308, which may include a screw joint. In a different embodiment, the popper 202 can be chemically bonded to a wall of the valve 302 or other vessel. However, in yet a different embodiment, the clamping surface of the popper 202 can be integrated (encompassed) with the wall of the valve 302 or any other vessel (see FIGS. 5A and 5B, for example).

In a preferred embodiment, after the release of pressure, which causes a conformation change of the popper 202 (or more specifically, the membrane 204), the popper 202 returns to its closed upstream position. In other words, the popper 202 preferentially reverts back to the conformation illustrated in FIGS. 3A and 3B. Of note, the popper 202 in a closed upstream position has a global energy minimum. Further, when the valve is in an open downstream position, the popper 202 has a local energy minimum. Additionally, there is a finite amount of energy required to change the popper 202 from the closed upstream position to an open downstream position. The term used to describe the ability of the popper 202 to prevent the flow (impermeable) in one conformation (or configuration) and to permit flow (permeable) in another conformation is dynamic permeability (DP). Further, as shown in FIGS. 3A and 3C, the popper 202 can be positioned in a valve 302 so to extend entirely across the cross sectional area of flow through the valve 202.

Of note, the popping pressure required to cause the popper 202 to undergo a conformation change can be a function of geometric parameters of the popper 202, a function of the material properties of the material forming the popper 202 as well as a function of the geometric parameters of the popper 202 alone or a function of the material properties of the material forming the popper 202 alone. The geometric parameters of the popper 202 can include thickness of the membrane 204, thickness of the brim 206, and internal radius of the membrane 204 as well as the shape of the opening 310, positioning (orientation) of the opening 310, the size of the opening 310, and the number of slits an opening 310 may have. The material properties of the material forming the popper 202 can include the material's Young's modulus, elasticity, resiliency, shore hardness, stiffness, and yield strength as well as Poisson's ratio. In this way, a popper 202 can be manufactured to meet a set of specific requirements, including a specific popping pressure (the pressure at which the popper 202 undergoes the conformation change). In other words, the popper 202 can be manufactured to have a specific opening pressure value and closing pressure value.

More specifically, a popper 202 can be designed and manufactured to have specific geometric parameters and/or material properties resulting in the popper 202 having a specific popping pressure. In particular, a correlation exists between thickness (of the membrane 204) of the popper 202 and the opening and closing pressures, such that a popper 202 having a larger thickness can have a larger opening and closing pressure than a popper 202 with a smaller thickness. Similarly, there is a relationship between material properties and popping pressure, such that a softer material (smaller shore hardness value) has a lower opening pressure and harder materials have a higher opening pressure. Additionally, there is an inverse relationship between the diameter of the popper 202 and valve pressure, such that in a preferred embodiment, a softer material and/or smaller thickness can be preferred at smaller radii to maintain the low-pressure range required for cerebral shunts. In this way, a specific popping pressure can be achieved for the popper 202 such that when the upstream pressure driving the flow of the CSF in the valve 302 is at or below the popping pressure, the popper 202 is in a closed position, i.e. not allowing CSF to flow through the popper 202, but when the upstream pressure driving the flow of the CSF in the valve 302 is above the popping pressure the popper 202 is in an open position, i.e. allowing CSF to flow through the popper 202 and the valve 302. In a preferred embodiment, the opening pressure or popping pressure of the popper 202 can be in a range of about four to twenty millimeters of mercury (4-20 mmHg), and preferably in a range of about eight to twelve millimeters of mercury (~8-12 mmHg), which causes the popper 202 to change its configuration from closed to open. However, it is important to note that the popping pressure is also dependent on the pressure exerted on the distal surface 224 of the popper 202. The pressure on the distal surface depends on the pressure at the placement location of the distal end of the distal catheter, which may be placed in the peritoneal cavity, the heart, or other suitable locations. The pressure within the peritoneal cavity may be in a range of between zero to four mmHg, but the downstream pressure may be different depending on where the distal end of the distal catheter is placed. Downstream pressure in the peritoneal cavity may even be negative for example, when a patient is upright. In other words, in one embodiment, once the pressure of the upstream CSF (pressure on the proximal surface 208) reaches or exceeds an upper threshold that can be in the range of eight to sixteen mmHg, so that the pressure across the membrane 204 can be at or above about eight to twelve mmHg (if the distal end of the distal catheter is placed in the peritoneal cavity), the membrane 204 undergoes a configuration change (to open). It is specifically contemplated that the pressure across the membrane 204 required to open the membrane may be different depending on where the distal end of the distal catheter is placed. A popper 202 may be specifically manufactured to pop with higher or lower pressure across the membrane 204 depending on the desired maximum upstream pressure and the anticipated downstream pressure. Different poppers can be manufactured to pop with different pressure across the popper by varying the material used and the dimensions of the popper. However, in an embodiment, once the upstream pressure of the CSF (pressure on the proximal face) falls to about ten millimeters of mercury (~10 mmHg) (or, more specifically, the pressure across the membrane 204 falls below about 4-10 mmHg, when the downstream pressure is about 0-6 mmHg), the membrane 204 again undergoes a configuration change from open to closed. Of note, in different embodiments the popping pressure of the popper 202 can range from about five millimeters of mercury to about twenty millimeters of mercury (~5-20 mmHg). Of note, the popper 202 can have both a different opening pressure (value) and closing pressure (value) or the popper 202 can have the same opening pressure (value) and closing pressure (value). In the preferred embodiment for cerebral shunting, the opening and closing pressures are each in the range of about 5-20 mmHg.

In alternate applications, a valve 302 with an optional sensing mechanism can be placed in series with an additional cerebral shunt valve, with the valve 302 and the sensing mechanism placed downstream of the additional cerebral shunt valve within the cerebral shunt system 104, or within the distal catheter 120, or at an end (not the end coupled to a flow valve of the cerebral shunt) of the distal catheter 120. Regardless of where the popper 202 is placed, the membrane 204 can undergo a conformation change from closed to open based on the pressure differential that drives the flow of CSF: a pressure in the brain (5 through 15 mmHg (millimeters of mercury)) and a pressure in the peritoneal cavity (4 through 6 mmHg). More specifically, the popper 202 deforms into a downstream position (open configuration) draining CSF continuously as long as the difference between the pressures experienced at the proximal surface 208 and distal surface 224 of the membrane 204 is above the opening pressure of the popper 202, whereas the popper 202 maintains its upstream position (typically a closed configuration) and, thus, preventing drainage, if the pressure difference across the membrane 204 is below the opening pressure of the membrane 204. In other words, the membrane 204 is pneumatically activated by a popping pressure value (triggering pressure value or opening pressure) that is a function of the geometry of the popper 202 and the material used in the popper 202 (or more specifically, the properties of the material(s) used in the popper 202). When the popping pressure value is reached and/or exceeded, the membrane 204 will undergo a deformation, inversion, or snap through buckling event from the configuration shown in FIG. 3A to the configuration shown in FIG. 3C. The resulting deformation also enables one-way flow of CSF through the opening 310 (see FIGS. 3D and 3E). It is the deformation of the membrane 204, which is a displacement that can be measured by a sensing mechanism, which enables an inference as to whether or not the membrane 204 moves between the closed position and open position, and therefore whether there is or is not flow of CSF through the valve 302.

Of further note, the popper 202 illustrated in FIGS. 3B and 3D represent the same popper. FIG. 3E represents an alternate embodiment with a different shape of opening. As such, the membranes of these figures define an opening 310, though it is not shown in FIG. 3B. In other words, there is no visual opening 310 present in the popper 202 of FIG. 3B, as the popper 202 illustrated in FIG. 3B is in the closed conformation, and therefore is impermeable and the "opening" remains closed. Additionally, FIG. 3E illustrate the resulting opening when there are four spokes (formed by two slits) oriented as shown in FIG. 4A.

Figure 4A:
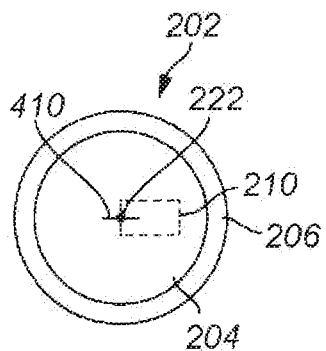
FIGS. 4A, 4B, 4C, 4D, 4E, and 4F are plan views illustrating different placements and shapes of openings defined by a popper.
Figure 4B:
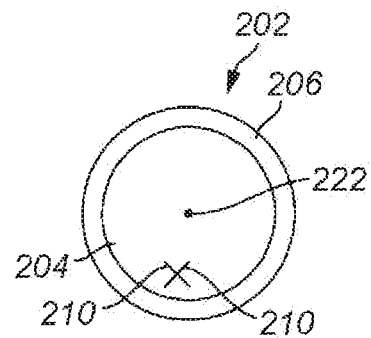
Figure 4C:
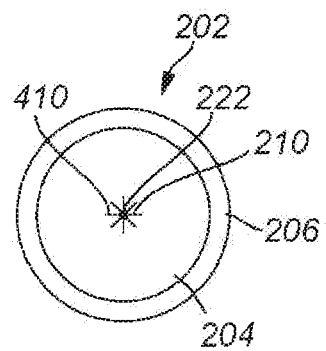
Figure 4D:
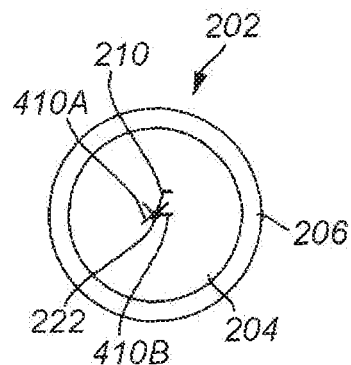
Figure 4E:
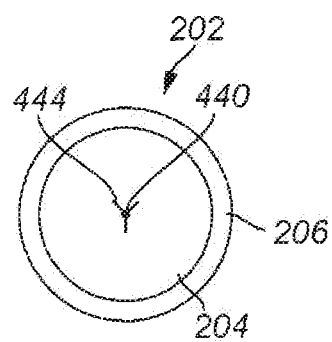
Figure 4F:
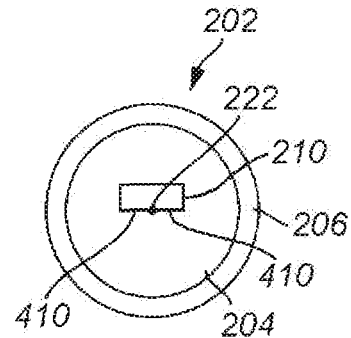

FIGS. 4A, 4B, 4C, 4D, 4E, and 4F are plan views illustrating different placements and shapes of openings defined by a popper. In other words, as explained herein, the opening 310 illustrated in FIG. 3D can include zero or more spokes 410 extending from the apex 222, where the spokes 410 can vary in terms of shape, size, orientation (positioning) and/or the number of spokes 410. More specifically, the poppers 202 illustrated in FIGS. 4A through 4F each have a brim 206 surrounding the membrane 204. Further, the membrane 204 of each popper 202 includes an apex 222, which is defined as being at the highest point of the membrane 204. Further, each popper 202 can define an opening (as shown in FIG. 3D) that is defined by zero or more slits 210 or spokes 410. In other words, in one embodiment, there can be an opening that includes zero slits 210 or spokes 410, but instead is just an opening, similar to what is pictured in FIG. 3D. In one embodiment, this opening can be formed using a pin or die. In a different embodiment, there can be a single slit 210 (−), not shown, which in one embodiment can be formed using a precision knife, such as an X-ACTO knife. There can also be two spokes 410, formed by a single slit 210 as shown in FIG. 4F. In a preferred embodiment, there can be four spokes 410 (+), formed by two single slits 210, as illustrated in FIG. 4A. As shown in FIG. 4B, there can be a different embodiment having two slits 210, positioned not at the apex 222, but off centered. There can also be six spokes 410 (*), comprising three single slits 210, as shown in FIG. 4C. Yet further, the opening can include three spokes forming a "Y" that can include three single slits, as shown in FIG. 4E. Yet further, the opening can include two spokes 410 forming a "V" (not illustrated), which can be formed by making two slits 210. In addition to using a precision knife, the slit(s) 210 and spokes 410 can also be formed by laser cutting, or by any method now known or later developed. Of note, though embodiments having specific number of spokes 410 and/or slits 210 are illustrated, it should be understood that any number of spokes 410 and/or slits 210 may be present. Of further note, the spokes 410 (and slits 210) are used to induce dynamic permeability in the membrane 204. Further, as noted below, the slits 210/spokes 410 may be linear, curved or angular, and also may intersect at even or unevenly spaced angular intervals. Yet further, though the spokes 410 and slits 210 can be of any length, in a preferred embodiment, neither the spokes 410 nor the slits 210 are longer than twice the thickness of the membrane 204 of the popper 202. In other words, the length of the spokes 410 and the slits 210 can be less than twice the thickness of the membrane 204.

Further, the positioning (orientation) of the slits 210 and/or spokes 410 can vary. For example, in the preferred configuration, as shown in FIGS. 4A, 4C, and 4D, the spokes 410 can originate from the apex 222 of the membrane 204. In other words, the spokes 410 can be oriented so as to be centered on (around) the apex 222 of the membrane 204. In a different embodiment, as shown in FIG. 4B, the slits 210 can positioned anywhere on the membrane 204. Additionally, the slits 210 and/or spokes 410 can be linear as shown in FIGS. 4A, 4B, 4C, and, in part, 4D; but the slits 210 and/or spokes 410 can also be bent or curved as illustrated in FIG. 4D (which illustrates only the spokes 410 being bent or curved). Of note, the spokes 410 that are curved can include one or more changes in angle or concavity. Additionally, the slits 210 and/or spokes 410 can be evenly spaced. In other words, the slits 210 (and spokes 410) shown in FIG. 4A can be configured to be perpendicular to each other, so that there is about a ninety-degree (90°) angle between each of the slits 210. In a different embodiment, the angle between the slits 210 can be approximate sixty degrees (60°), as illustrated in FIG. 4C. Further, the angle (or distance) between the spokes 410, as shown in FIG. 4D between spoke 410A and 410B, can be non-even. Of note, a slit 210 references an opening on the same line, whereas a spoke 410 references an opening extending from an apex 222. For example, FIG. 4B illustrates slits 210, but not spokes 410, because the opening is not extending from an apex 440, whereas FIG. 4A pictures two slits 210 comprising a total of four spokes 410.

Figure 5A:
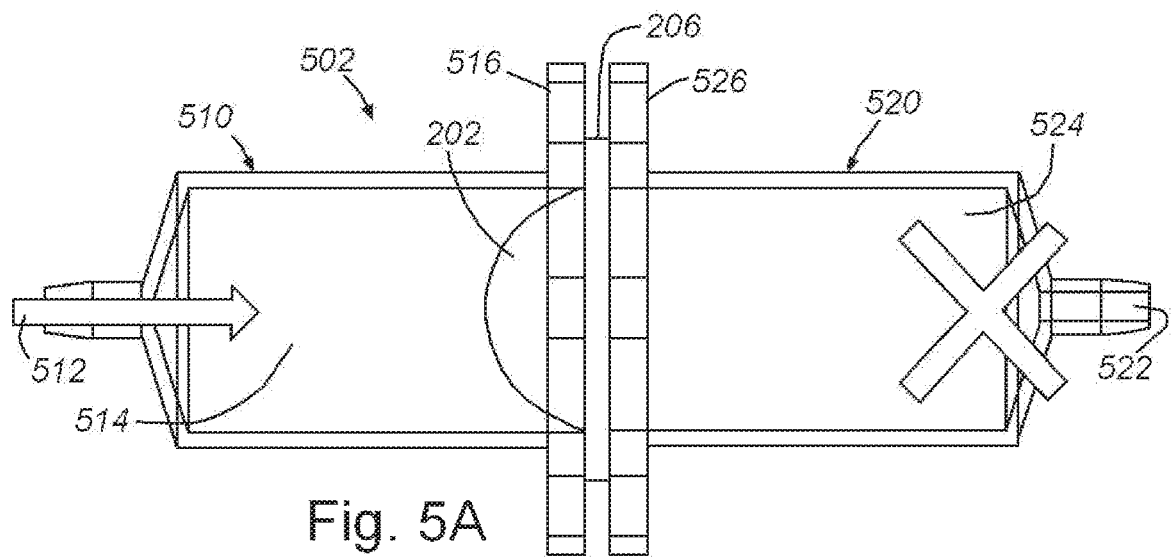
FIG. 5A is a cross section view of an alternate embodiment of an exemplary valve with the popper of FIG. 2A shown in closed conformation according to an embodiment.

FIG. 5A is a cross section view of an alternate embodiment of an exemplary valve with a popper of FIG. 2A shown in closed conformation according to an embodiment. Valve 502 can include a proximal shell 510, the popper 202, and a distal shell 520. The proximal shell 510 can include a proximal inlet 512, a proximal chamber 514, and an annular proximal plate 516. The proximal inlet 512 can be in fluid communication with the proximal catheter 112, so that CSF 106 can flow from ventricle 110 through the proximal catheter 112, through the proximal inlet 512, and into the proximal chamber 514. The distal shell 520 can include a distal outlet 522, a distal chamber 524, and an annular distal plate 526. The distal outlet 522 can be in fluid communication with the distal catheter 120. The brim 206 can be held between the proximal plate 516 and the distal plate 526, thereby creating an annular seal between proximal shell 510 and distal shell 520. The popper 202 is shown in a closed conformation with a relaxed dome-shaped membrane 204 extending proximally out of the plane of the brim 206 and into the proximal chamber 514. With the popper in this closed conformation, CSF 106 can be prevented from flowing out of the proximal chamber 310 into the distal chamber 316, thereby preventing CSF 106 from draining out of the brain 108.

Figure 5B:
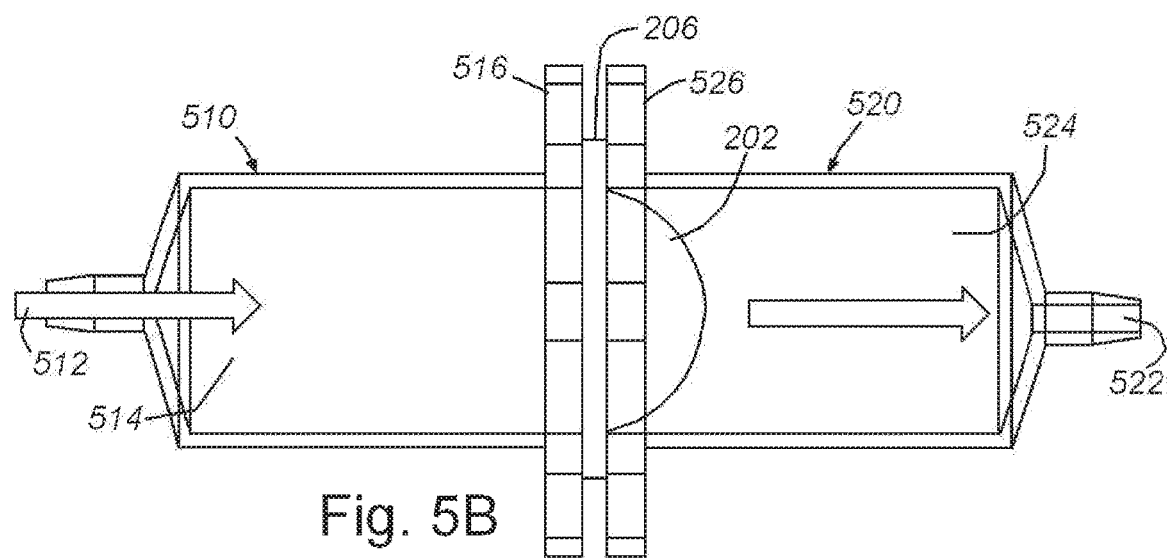
FIG. 5B is a cross sectional view of the exemplary valve of FIG. 5A with the popper of FIG. 2A shown in an open conformation according to the embodiment, when upstream fluid pressure exceeds the opening pressure of the popper of FIG. 2A.

FIG. 5B is a cross sectional view of the alternate embodiment of the exemplary valve of FIG. 5A with a popper of FIG. 2A shown in an open conformation according to the embodiment, when upstream fluid pressure exceeds the opening pressure of the popper of FIG. 2A. When the popper 202 is in the inverted, open conformation, the membrane 204 is inverted and can extend distally out of the plane of the brim 206 and into the distal chamber 524. However, it is specifically contemplated that alternate embodiments may include a thicker brim 206, so that the inverted membrane 204 may not fully extend distally out of the plane of the brim 206. In the inverted, open conformation with the slits 210 flexed opened creating an opening 310, CSF 206 is allowed to flow from the proximal chamber 514 through the opening 310 and into the distal chamber 524 where it can then flow out of the distal chamber 524 through the distal outlet 522 and into the distal catheter 120, thereby decreasing the volume of the CSF 106 in the brain 108 and reducing the CSF pressure within the patient's skull.

Figure 6A:
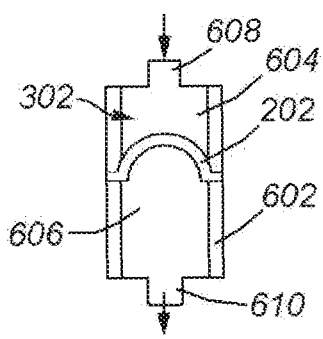
FIGS. 6A, 6B, 6C, and 6D are cross sectional views of the popper situated in different embodiments of a valve in series with the flow of a substance along a fluid transmission line.
Figure 6B:
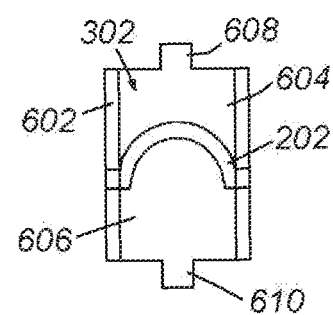

FIGS. 6A, 6B, 6C, and 6D are cross sectional views of the popper situated in different embodiments of a valve in series with the flow of a substance along a fluid transmission line. More specifically, FIGS. 6A, 6B, 6C, and 6D illustrate a popper 202 being situated in various embodiments of a valve. Of note, it is contemplated that, for medical applications involving a cerebral shunt, the valve with one or more poppers 202 situated within can be placed at the skull (see FIGS. 6C and 6D), on the skull, in the peritoneal cavity, or other possible locations. Of note, FIGS. 6A, 6B, 6C, and 6D illustrate a popper 202 including a brim, and, in particular, FIGS. 6A and 6B show a valve 302 with the brim of the popper 202 clamped in place by the wall 602 of the valve 302. However, in a different embodiment, a popper 202 may have no brim. The placement of the popper 202 into the valve 302 results in the creation of two flow chambers 604 and 606 in the valve 302. The valve 609 further includes two connectors 608 and 610. Each of these connectors 608 and 610 can be coupled to a vessel, such as a catheter and/or a pipe, through which a substance, such as a liquid, a gas, and/or a slurry flow. More specifically, the connector 608 through which the incoming flow enters the valve 609 can be coupled to a ventricular catheter, where the connector 619 through which the flow exits the valve 609 can be connected to a distal catheter.

Figure 6C:
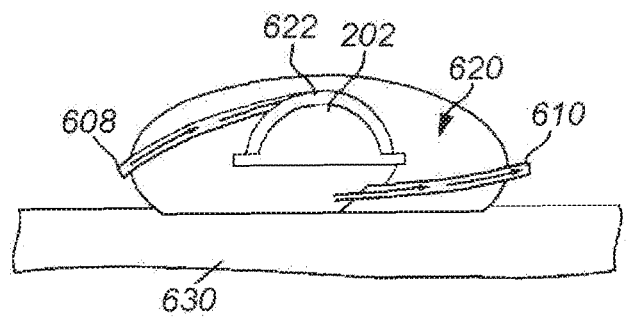
Figure 6D:
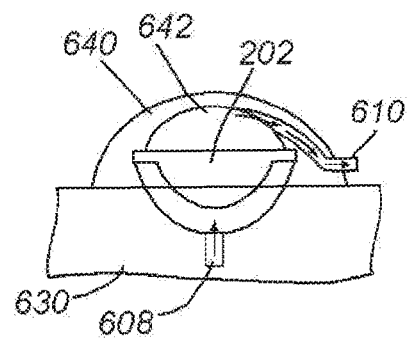

With respect to FIGS. 6C and 6D, FIG. 6C shows an alternate embodiment of a valve 620 with two opposing positioned connectors 608 and 610 sitting on the same axis and disposed above the surface of the skull 630, with the arrows indicating the direction of CSF flow. FIG. 6C further illustrates that the valve 620 has disposed within it an inner housing 622, which holds the popper 202. FIG. 6D illustrates yet another alternate embodiment of a valve 640 with connectors 608 and 610 that are positioned on different axes, where the valve 640 is partially inserted into the same burr hole where the ventricular catheter also penetrates the skull 630. FIG. 6D depicts popper 202 in an inverted position (but still initially in an upstream closed orientation) in an inner housing 642, which is disposed within the valve 640. Of note, the arrows pictured in FIGS. 6C and 6D illustrate the direction of flow; however, based on the current orientation of the popper 202 there would be no flow in the direction of the arrows, as the popper 202 pictured in both of these illustrations is current shown in a closed configuration. Additionally, though not pictured, a ventricular catheter could be attached to the connector 608 where the flow is entering the valve and a distal catheter can be coupled to the connector 610 where the flow is leaving the valve.

Figure 7A:
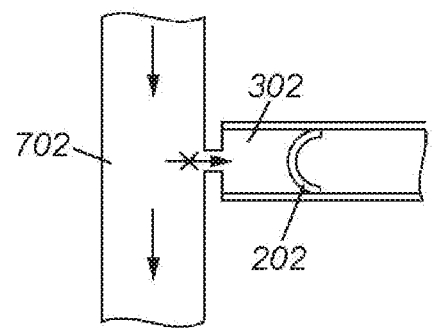
FIGS. 7A and 7B are cross sectional views of the popper situated in a valve in parallel with the flow where the valve is in the closed and open positions, respectively.
Figure 7B:
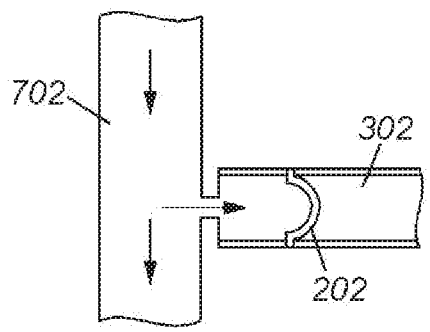

FIGS. 7A and 7B are cross section views of an embodiment of the popper 202 situated in a valve 302 parallel with a flow of a substance, such as a liquid, gas, or slurry, through a vessel, such as a pipe 702. More specifically, FIG. 7A illustrates that flow of the substance continues through pipe 702 and not through the popper 202 as long as the pressure in the pipe 702 remains less than the popping pressure value of the popper 202. However, once the pressure in the pipe 702 meets and/or exceeds the popping pressure value of the popper 202, the membrane 204 inverts enabling any substance in the pipe 702 to now flow through the popper 202, thus relieving pressure in the pipe 702 by allowing any substance in the pipe 739 to flow through the valve 302. In other words, when a valve 302 is parallel, there can be more than one path of flow.

Because the valve can include means for detecting valve failure, explained more fully below, it is specifically contemplated that the valve with failure detection means can be used in conjunction with another cerebral shunt valve. By way of non-limiting example the popper 202 can be friction fitted into the tubing of the distal catheter 120, such that a seal is created, which prevents the flow of CSF at the boundary between the outside edge of popper 202 and the inside surface of the distal catheter 120. In a different embodiment, a valve with a popper 202 can be placed in parallel, such that there is more than one path of flow (see FIGS. 7A and 7B). In yet a further embodiment, the popper 202 can be placed anywhere along a fluid stream (where the CSF can flow, such as in any component of a cerebral shunt).

In addition to popper 202, a valve can include a sensing mechanism. The sensing mechanism in conjunction with the popper 202 is used to identify a blockage in the cerebral shunt 104. More specifically, the membrane 204 inverts into a downstream position (open configuration) draining CSF continuously as long as the difference between the pressures experienced at the proximal surface 208 and distal surface of the membrane 204 are above the opening pressure of the membrane 204, whereas the membrane 204 maintains its upstream position (typically a closed configuration) and, thus, prevents drainage, when the pressure difference across the membrane 204 is below the closing pressure of the membrane 204. Thus, if a patient suffers a cerebral shunt blockage, whether upstream in the ventricular catheter 112, at the flow valve itself, or downstream in the distal catheter 120, the popper 202 will fail to open, and will remain closed as long as the blockage remains in place. As such, in one embodiment, the sensing mechanism, which can be part of the valve, can be used to determine whether the popper 202 is in the upstream closed position or downstream open position at a given time. The information collected by the sensing mechanism regarding the position of the popper 202 at a given time can be stored locally and sent to a computer, such as when the sensing mechanism is in range of a computer's wireless signal, using BLUETOOTH, for example, though any wireless communication standard now known or later developed can be used. This information can be used to show that the popper 202 is closed indefinitely. In other words, if there is a blockage anywhere along the cerebral shunt 104, the popper 202 will fail to open and the sensing mechanism will show (based on the data collected) that the popper 202 is closed indefinitely, indicating a blockage. Of note, once a blockage has been indicated, a clinical maneuver such as coughing or baring down can be performed to intentionally temporarily elevate the ICP. If the sensor mechanism does not detect a popper 202 opening during these elevated pressure procedures, a cerebral shunt blockage can be confirmed.

Yet further, the sensing mechanism can utilize optical mechanisms, electrical mechanisms, and/or mechanical mechanisms to detect a blockage by sensing changes in the mechanical, geometric, optical, material, electrical, and/or electromagnetic properties of the popper 202. More specifically, in one embodiment, the sensing mechanism can include a sensor that detects a conformation change of the popper 202, a battery, an LED light source, a photo detector (a sensor), a microcontroller that processes a signal from the photo detector (a sensor), memory to store the signal from the sensor, a radio frequency (RF) transceiver and receiver. In another embodiment, the sensing mechanism can include an infrared (IR) sensing method, a battery, memory to store the signal from the sensor, a radio frequency (RF) transceiver and receiver, with the popper 202 (a bi-stable structure) serving as an IR photo interrupter or photo reflector. Of note, the device can further include an additional element, such as an external device (outside the patient with a cerebral shunt) that can obtain the data captured by the sensing mechanism and, thereafter, be accessed by medical personnel and/or the patient, so that the medical personnel and/or patient can review the captured data. In yet a different embodiment, once the sensing mechanism detects a blockage by detecting an absence of changes in the mechanical, geometric, optical, material, electrical, and/or electromagnetic properties of the popper 202, a message can be transmitted from the sensing mechanism to a receiving device that can further process the message. In other words, once the sensing mechanism detects a conformation change or an absence of a conformation change of the membrane 204 of the popper 202, an electronic message can be sent from the sensing mechanism via a read out unit over a computer communications network to a receiving device (read in unit). The sensing mechanism may be located upstream of the popper 202, downstream of the popper 202, or both (see FIGS. 8A through 8D). Additionally, the position as well as orientation (open, closed, upstream, and/or downstream) of the popper 202 may also be sensed using an external imaging modality, such as ultrasound, magnetic resonance imaging (MM), and computed tomography (CT).

Figure 8A:
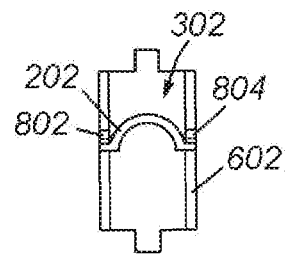
FIGS. 8A, 8B, 8C, and 8D are cross sectional views of alternate embodiments of valves illustrating potential locations of one or more sensor components associated with the sensor mechanism.
Figure 8B:
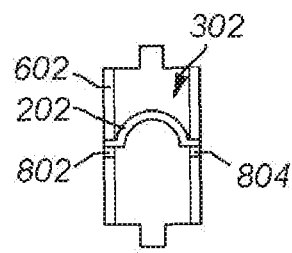
Figure 8C:
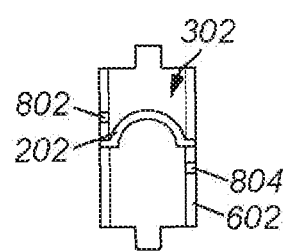
Figure 8D:
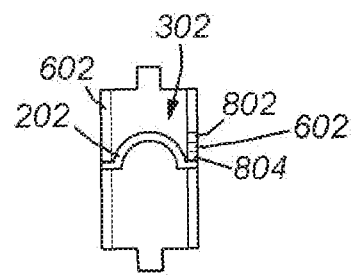

FIGS. 8A, 8B, 8C, and 8D are cross sections of alternate embodiments of valves illustrating potential locations of one or more sensor components associated with the sensor mechanism. More specifically, FIGS. 8A, 8B, 8C, and 8D picture a popper 202 situated in a valve 302, with two sensor components 802 and 804, each being coupled to a wall 602 of the valve 302. Sensor components 802 and 804 could be embedded in the wall 602, glued to the wall 602, mounted through the wall 602, or otherwise fixed in place. In an embodiment, sensor component 802 can be an LED light and sensor component 804 can be a photo detector. In an alternate embodiment, sensor component 802 can be an infrared emitter, and sensor component 804 can be an infrared detector. Other wavelengths are specifically contemplated. In another alternate embodiment, a single sensor component could be a mechanical sensor capable of detecting a conformation change of the popper 202. One or more mechanical sensors may be used. In another alternate embodiment, a single sensor component could detect electrical and/or electromagnetic properties of the popper 202, and one or more sensor components may be used. In particular, both sensor components 802 and 804 can be positioned above the popper 202 as shown in FIG. 8A; both sensors 802 and 804 can be positioned below the popper 202, as illustrated in FIG. 8B; one sensor component 802 can be positioned above the popper 202 and a different sensor component 804 can be positioned below the popper, as pictured in FIG. 8C; and as illustrated in FIG. 8D, both sensor components 802 and 804 can be located on the same side above the popper 202. It is further contemplated that both sensor components 802 and 804 can be located on the same side below the popper 202 (not pictured). Of note, though FIGS. 8A through 8D illustrate a popper 202 with a brim, the popper 202 can also be of a type without a brim, such as a popper that is integrally manufactured with the valve 801 (or vessel). Of further note, though two sensor components 802 and 804 are pictured in each of FIGS. 8A through 8D, the sensing mechanism can include one sensor, such as explained below in FIGS. 9A and 9B.

Of note, with respect to the sensor components, in an embodiment one sensor component can be a source and the other sensor component can be a detector. More specifically, if the sensing mechanism employs an optical mechanism, one of the sensor components can be a (light) emitter, such as a light emitting diode (LED) source while the other sensor component can be a detector, such as a phototransistor. In addition to a LED-based sensor system, other sensors based on different detection options, such as radio frequency identification (RFID), IR, one or more magnetic switches, one or more mechanical switches, one or more fiber optic cables, sensors measuring capacitance, sensors measuring resistance, one or more electrodes, and/or one or more variable bending resistors may be used.

In one embodiment of a LED-based sensing mechanism, a LED acting as one sensor component 802 can be positioned upstream from the popper 202 on one side of a valve 302 (containing the popper 202) and a phototransistor can act as a second sensor component 804 and be positioned on the opposite side of the valve 302 directly opposite the first sensor component 802 (as shown in FIG. 8A). Both sensor components can be positioned at a distance upstream from the popper 202 that is no greater than the outer radius OR of the membrane of the popper 202. By way of non-limiting example, the LED can flash across the fluid chamber every second for a duration of one millisecond. When the popper 202 is in the open (downstream) configuration, the light from the LED 802 travels through the CSF, across the flow chamber, striking the phototransistor 804 on the opposite wall of the fluid chamber. However, when the popper 202 is in a closed position, the popper 202 blocks the light from the LED 802, keeping the phototransistor 804 from detecting the light. Because when functioning normally, a popper 202 is expected to open and close (change configurations) a number of times per day, a blockage can be detected when the popper 202 fails to open. In particular, the sensing mechanism (including, in part, the LED source and corresponding detector (the phototransistor)) will detect that the popper 202 is in a closed position indefinitely, indicating a blockage.

Figure 9A:
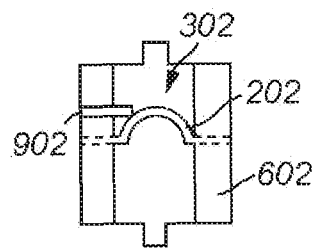
FIG. 9A is a cross sectional view of an alternate embodiment of a valve with a protruding sensor from a wall of a valve to sense the popper.

FIG. 9A is a cross section view of another alternate embodiment of a valve with a sensor 902 protruding from the wall 602 of the valve 302 to sense the popper 202. The sensor 902 can be attached directly to the wall 602 or to another element (not shown) attached to the wall 602, which enables the sensor 902 to extend inwardly from the inner wall 602 of the valve 302. As explained below, when the pressure in a valve or other vessel containing the popper 202 meets or exceeds an opening pressure value of the popper 202, the popper 202 deforms, resulting in the popper 202 no longer maintaining contact with the sensor 902, and also enabling the flow of the substance through the popper 202. As such, the deformation of the popper 202 can be detected by a sensor 902 of the sensing mechanism based upon the lack of physical contact of the popper 202 with the sensor 902. More specifically, in one embodiment, the sensor 902 can be a pressure sensor which detects a change of pressure (whether an increase or a decrease in pressure) depending on when the popper 202 (or a protrusion 904 of the popper 202, as shown in FIG. 9B) is or is not touching the sensor 902.

Figure 9B:
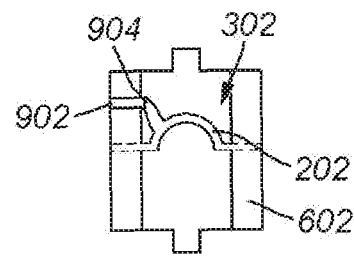
FIG. 9B is a cross sectional view of an alternate embodiment of a valve with a protrusion extending out from a popper for use in the detection of a configuration change of the popper.

FIG. 9B is a cross section view of another alternate embodiment of a valve with a protrusion 904 extending out from a popper 202 for use in the detection of a configuration change of the popper 202. More specifically, FIG. 9B shows an alternate embodiment of a popper 202 with a nipple or (wart-like) protrusion 904 extending from the proximal surface of the popper 202 positioned in a valve 302. As shown in FIG. 9B, when the popper 302 is in a relaxed, closed positioned, e.g. when there is no flow through the popper 302, the protrusion 904 is in physical contact with the sensor 902, which is coupled to the wall 602 of the valve 302. However, when the pressure on the upstream, proximal side of the popper 202 meets or exceeds the popping pressure value of the popper 202, the popper 202 deforms, resulting in the protrusion 904 no longer maintaining contact with the sensor 902, and also enabling the flow of the substance through the popper 202. As such, the deformation of the popper 202 can be detected by a sensor 902 of the sensing mechanism based upon the lack of physical contact of the protrusion 904 with the sensor 902.

Figure 10:
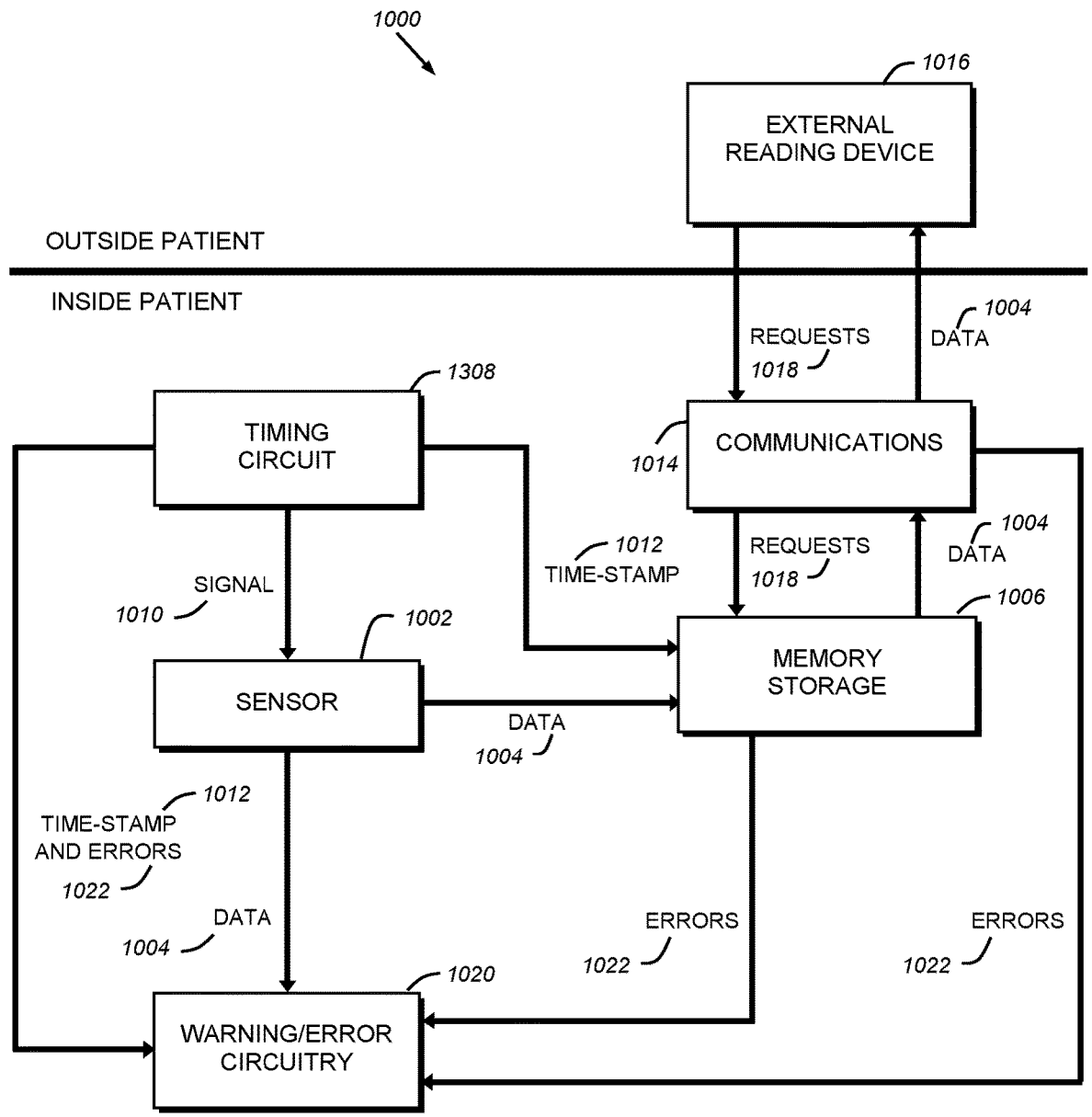
FIG. 10 is a system diagram showing an embodiment of cerebral shunt valve monitoring system.

FIG. 10 is a system diagram showing one possible embodiment of a cerebral shunt valve monitoring system 1000. In the event of a cerebral shunt valve failure, the pressure of the CSF 106 increases over time, and may result in damage to the brain or even death of the patient. At least one sensor 1002 can be used to collect data 1004 regarding the operation and/or failure of the cerebral shunt valve. In regards to FIG. 10, sensor 1002 can be a single sensor such as a mechanical sensor, or a system of sensor components such as light emitters and photo detectors, or a combination of various sensing mechanisms. The sensor 1002 can monitor the movement of the membrane 204. The sensor 1002 can include a variable bending resistor that can sense the movement of the membrane between the relaxed, open conformation and the inverted, closed conformation. In this embodiment, the data 1004 that is collected can be binary, yes-or-no data indicating if the membrane has moved into the inverted, closed conformation. Similarly, in another embodiment a light emitter and an optical sensor can used to determine if the membrane has moved into the inverted, open conformation, and the data 1004 can be a binary data. In alternate embodiments, various sensor systems, alone or in combination, can be used to monitor the movement or absence of movement of the membrane 204 and provide useful data 1004.

Sensor 1002 can output data 1004 to a memory storage 1006 that can be implanted within the patient and can collect data 1004 from the sensor. System 1000 can include a timing circuit 1008 that can send a signal 1010 to the sensor 1002 triggering the sensor to collect data 1004. The sensor can be switched "off" most of the time, and can be switched "on" in response to a triggering signal 1010, and can then collect data 1004, output that data to the memory storage 1006, and then switch back to "off." The timing circuit 1008 can also send a time-stamp 1012 to the memory storage 1006, so that data 1004 being output by the sensor 1002 can be associated with a time-stamp 1012. System 1000 can include a communication device 1014 that can be implanted within the patient and can communicate with an external reading device 1016 that can be outside of the patient. Communication device 1014 and external reading device 1016 can communicate with each other using radio frequency, near infrared light, or other means. The external reading device 1016 can communicate a request 1018 to the communication device 1014. Communication device 1014 can then output that request 1018 to the memory storage 1006. In response to the request 1018, memory storage 1006 can output data 1004 that can include time stamps 1012 to the communication device 1014. Communication device 1014 can then communicate the data 1006 to the external reading device 1016. The external reading device 1016 can be a device used by a doctor to verify that the valve is functioning properly. The external reading device can also be a device used by the patient or the patent's caregiver to verify that the valve is functioning properly.

System 1000 can also include warning/error circuitry 1020 that can help to warn the patent or the patent's caregivers of any potential problems or malfunctions. The warning/error circuitry 1020 can emit an alert that may consist of audible beeps, a phone notification, or other methods that can be used to warn a patent that they need to go see their doctor. Sensor 1002 can output data 1004 to the warning/error circuitry 1020 so that indications of a problem such as elevated pressure can trigger the warning/error circuitry 1020 to emit an alert. Memory storage 1006 can also output errors 1022 to the error/warning circuitry 1020 such as broken memory storage, low battery, or a predetermined number of consecutive data points indicating that the membrane 204 is in the closed conformation, or other indicators of low flow rate, blockage, or valve failure. The timing circuit 1008 can also send errors 1022 and/or time-stamps 1012 to the warning/error circuitry 1020. Communications device 1014 can also send errors 1022 to the warning/error circuitry 1020 so that the patient can be apprised of any problems before they become life-threatening. A battery is also provided but not shown to provide power to the elements of the system 1000 that are implanted within the patient 102. Warning/error circuitry 1020 can also emit an alert if the battery becomes low. This system is thereby able to monitor the functioning of the valve, and provide data regarding that functioning to a doctor, as well as providing an alert if the patient may need to visit a doctor. This alert can be emitted before the pressure of the CSF 106 builds up to a level that trigger physical symptoms in a patient. By alerting a patent or the patient's caregiver to a potential problem before the patient has observable symptoms, injury to the brain or death of the patient can be avoided.

Of note, though the popper and valve are largely described herein as being integrated with a cerebral shunt, it is also contemplated that the valve can be used in other applications, such as detecting blockage in a vessel while monitoring the flow of liquids and/or gas through pipes in a house or industrial setting. The valve with a sensor can also be used for monitoring a flow of liquids during medical intravenous fluid therapy (IV) for providing fluids, medicines or other medical applications. More specifically, a valve with a popper for detecting a blockage in a vessel, such as a pipe, can be provided. The popper can include a membrane having two configurations: a first configuration preventing a flow of a substance, such as a gas or liquid, through the membrane and a second configuration permitting the flow of the substance through an opening defined by the membrane in the second configuration. The membrane can change from the first configuration to the second configuration when a pressure of the substance on the upstream, proximal side of the popper meets or exceeds a popping pressure value of the membrane.

The foregoing has been a detailed description of illustrative embodiments of the disclosure. Various modifications and additions can be made without departing from the spirit and scope of this disclosure. Features of each of the various embodiments described above may be combined with features of other described embodiments as appropriate in order to provide a multiplicity of feature combinations in associated new embodiments. Furthermore, while the foregoing describes a number of separate embodiments of the apparatus of the present disclosure, what has been described herein is merely illustrative of the application of the principles of the present disclosure. For example, in various embodiments, the thickness of the membrane may vary and be thicker near the slits and thinner near the brim, or thinner near the slits and thicker near the brim. Or in alternate embodiments, when the membrane is viewed in cross section the slits through the membrane may not appear as straight lines that cut perpendicularly through the membrane, but may be at angles other than perpendicular, or may be "C" shaped, "S" shaped, appear as a sideways "V," or other possible variations. Additionally, as used herein various directional and dispositional terms such as "vertical", "horizontal", "up", "down", "bottom", "top", "side", "front", "rear", "left", "right", and the like, are used only as relative conventions and not as absolute directions/dispositions with respect to a fixed coordinate space, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances of the system (e.g. 1-5 percent). Accordingly, this description is meant to be taken only by way of example, and not to otherwise limit the scope of this disclosure.

What is claimed is:

1. A cerebrospinal fluid valve popper comprising:
a resilient membrane configured to deflect to cerebrospinal fluid, the resilient membrane having at least one pore extending between a first side of the membrane and a second side of the membrane, wherein when a fluid facing the first side of the membrane is at a first fluid pressure, the membrane is in a first conformation wherein the first side of the membrane is convex and the at least one pore is closed, and wherein when the fluid facing the first side of the membrane is at a second fluid pressure greater than the first fluid pressure, and the second fluid pressure facing the first side of the membrane is greater than a third fluid pressure facing the second side of the membrane, the membrane flexes to a second conformation wherein the first side of the membrane is concave and the at least one pore is open allowing the fluid to flow in a fluid flow direction from the first side to the second side through the membrane.

2. The valve popper of claim 1, wherein the membrane has a dome shape when the fluid facing the first side of the membrane is under the first fluid pressure.

3. The valve popper of claim 1, wherein a second side of the membrane is convex when the fluid facing the first side of the membrane is under the second fluid pressure.

4. The valve popper of claim 1, wherein when the fluid facing the first side of the membrane is under the second fluid pressure, the membrane flexes to the second conformation, and the at least one pore opens, so that the fluid flows through the open pore to a second side of the membrane, whereby the pressure of the fluid facing the first side of the membrane drops to the first fluid pressure so that the membrane returns to the first conformation, the first side of the membrane becomes convex, and the at least one pore becomes closed.

5. The valve popper of claim 1, wherein the at least one pore is defined by at least two slits that intersect each other in the first conformation, and form an opening in the second conformation.

6. The valve popper of claim 1, wherein a thickness of the resilient membrane varies between an apex of the resilient membrane as compared to a base of the resilient membrane.

7. The valve popper of claim 1, wherein the at least one pore defines zero or more spokes.

8. The valve popper of claim 1, wherein the fluid is in contact with the second side of the resilient membrane in the first conformation.

9. The valve popper of claim 1, wherein the resilient membrane is impregnated with an antibiotic.

10. The valve popper of claim 1, wherein a difference between the first conformation and the second conformation of the membrane can be monitored with an ultrasound or other imaging device.

11. The valve popper of claim 1, wherein the membrane has a local energy minimum when the membrane is in the second conformation.

12. The valve popper of claim 1, wherein the second fluid pressure is greater than a predetermined triggering pressure and the first fluid pressure is less than the predetermined triggering pressure.

13. The valve popper of claim 12, wherein the flexing comprises a buckling of the resilient membrane and is induced at the predetermined triggering pressure.

14. A cerebrospinal fluid valve comprising:
a valve housing defining an upstream portion and a downstream portion; and
a popper between the upstream portion and the downstream portion, the popper comprising,
a resilient membrane configured to deflect to cerebrospinal fluid, the resilient membrane having at least one pore extending between a first side of the membrane and a second side of the membrane, the first side of the membrane facing towards the upstream portion, the popper forming a seal between the upstream portion and the downstream portion, wherein when a fluid facing the first side of the membrane is under a first fluid pressure, the membrane is in a relaxed state wherein the first side of the membrane is convex and the at least one pore is closed, and wherein when the fluid facing the first side of the membrane is under a second fluid pressure greater than the first pressure, and the second fluid pressure facing the first side of the membrane is greater than a third fluid pressure facing the second side of the membrane, the first side of the membrane is concave and the at least one pore is open allowing fluid to flow downstream through the membrane in a first fluid flow direction from the first side of the membrane to the second side of the membrane while the first side of the membrane is concave.

15. The valve of claim 14, wherein the membrane has a dome shape when the fluid facing the first side of the membrane is under the first fluid pressure.

16. The valve of claim 14, wherein the at least one pore is defined by at least two slits that cross each other in the first conformation, and form an opening in the second conformation.

17. The valve of claim 14, wherein when the membrane is in the second conformation and the fluid facing the first side of the membrane returns to the first fluid pressure, the membrane returns to the relaxed state wherein the first side of the membrane is convex and the at least one pore is closed.

18. The valve popper of claim 14, wherein when the membrane returns to the first conformation, the movement of the membrane causes fluid on the first side of the membrane to travel in a second fluid flow direction away from the membrane and into a tube attached to the upstream portion of the valve housing.

19. The valve of claim 14, wherein when the membrane returns to the first conformation, the movement of the membrane displaces a volume of fluid that is greater than the volume between the concave surface of the second side when the membrane is in the first conformation and a plane of a base of a dome shape of the membrane.

20. A cerebrospinal fluid valve popper comprising:
a resilient membrane configured to deflect to cerebrospinal fluid, the resilient membrane having at least one pore extending between a first side of the membrane and a second side of the membrane, wherein when a fluid facing the first side of the membrane is at a first fluid pressure at the at least one pore and across a surface of the first side of the membrane, the membrane is in a first conformation wherein the first side of the membrane is convex and the at least one pore is closed, and wherein when the fluid facing the first side of the membrane is at a second fluid pressure at the at least one pore and across the surface of the first side of the membrane, the second fluid pressure being greater than the first fluid pressure, the membrane flexes to a second conformation wherein the first side of the membrane is concave and the at least one pore is open allowing the fluid to flow in a fluid flow direction from the first side to the second side through the membrane.

* * * * *